United States Patent [19]

Lavene

[11] Patent Number: 5,608,600

[45] Date of Patent: Mar. 4, 1997

[54] METALLIZED FILM CAPACITOR WITH INCREASED DIELECTRIC BREAKDOWN VOLTAGE

[75] Inventor: Bernard Lavene, Ocean, N.J.

[73] Assignee: Electronic Concepts Inc., Eatontown, N.J.

[21] Appl. No.: 127,867

[22] Filed: Sep. 28, 1993

Related U.S. Application Data

[63] Continuation-in-part of Ser. No. 20,344, Feb. 19, 1993, abandoned.

[51] Int. Cl.$^6$ .............................. H01G 4/005; H01G 4/32; H01G 7/00
[52] U.S. Cl. .................. 361/303; 361/301.5; 361/273; 29/25.42
[58] Field of Search ................... 361/301.5, 303, 361/304, 305, 309, 323, 273; 29/25.42

[56] References Cited

U.S. PATENT DOCUMENTS

| | | | |
|---|---|---|---|
| 3,185,907 | 5/1965 | McKee et al. | 361/305 |
| 3,457,478 | 7/1969 | Lehrer | 361/304 |
| 3,585,468 | 6/1971 | Chertok | 361/301.5 |
| 3,602,770 | 8/1971 | McMahon | 361/11 |
| 3,628,108 | 12/1971 | Craig | 361/304 |
| 3,644,805 | 2/1972 | Heywang | 361/273 |
| 4,072,976 | 2/1978 | Harari | 361/273 |
| 4,306,274 | 12/1981 | Yamagiwa et al. | 361/304 |
| 4,320,437 | 3/1982 | Shaw et al. | 361/305 |
| 4,470,097 | 9/1984 | Lavene | 361/304 |
| 4,477,858 | 10/1984 | Steiner | 361/273 |
| 4,642,731 | 2/1987 | Shedigan | 361/319 |
| 4,685,026 | 8/1987 | Lavene | 29/25.42 |
| 4,719,539 | 1/1988 | Lavene | 361/307 |
| 4,926,862 | 5/1990 | Miyajima et al. | 428/419 |
| 5,262,920 | 11/1993 | Sakuma et al. | 361/305 |

FOREIGN PATENT DOCUMENTS

| | | |
|---|---|---|
| 607826 | 11/1960 | Canada . |
| 44710 | 2/1990 | Japan . |
| 311017 | 11/1992 | Japan . |

*Primary Examiner*—Bot L. Ledynh
*Attorney, Agent, or Firm*—Ratner & Prestia

[57] ABSTRACT

The present invention involves a metallized wound capacitor having increased dielectric breakdown voltage which includes first and second dielectric webs. A first electrode having first and second portions, where the first portion is between 5–300 Ohms/square, is metallized on the first face of the first web, to a width less than the width of the first web. A second electrode having first and second portions is metallized on the first face of the second web to a width less than the width of the second web. The first and second electrodes extend from opposing dielectric web longitudinal edges leaving respective bare margins along opposing edges on the respective webs. Each second portion has a width equal to the opposing bare margin less a predetermined tolerance and is thicker than its respective first portion.

20 Claims, 2 Drawing Sheets

METALLIZED FILM CAPACITOR WITH INCREASED DIELECTRIC BREAKDOWN VOLTAGE

This application is a Continuation-In-Part (CIP) of U.S. patent application Ser. No. 08/020344 filed on Feb. 19, 1993, now abandoned.

FIELD OF THE INVENTION

This invention relates to metallized dielectric wound capacitors and, more particularly, to wound capacitors in which the metallization varies in thickness.

BACKGROUND OF THE INVENTION

A standard metallized film capacitor widely known in the art is the wound capacitor. Wound capacitors are constructed by sandwiching a dielectric film such as polycarbonate, polypropylene or polyester film between metal electrodes (e.g., vapor deposited metal film). Once formed, the combination dielectric/metal material is wound to form a capacitor. Some specific examples of wound capacitors are found in the following: U.S. Pat. No. 4,320,437 (Shaw etal.), U.S. Pat. No. 4,719,539 (Lavene), and U.S. Pat. No. 4,685,026 (Lavene).

In making wound capacitors and particularly pulse and AC wound capacitors, a problem has been in forming the lead termination. The ends of the wound capacitor have been sprayed with molten metal particles to form terminals engaging the electrodes metallized on the dielectric web. Leads have been bonded to the terminals. In order to decrease the ESR (equivalent series resistance), decrease the dissipation factor and increase the reliability of the connection between the metallization and the spray, it has been crucial to have a substantial amount of metallization defined at the capacitor end, since it is such metallization which is in electrical connection with the metal spray. The art has sought a high quality connection with as low resistance as possible. This is particularly important with thin film dielectrics and low voltage capacitors requiring low losses and low ESR.

In order to assure at least one thickness of metallization at each capacitor end the dielectric webs have been offset one from the other. This has been particularly important in view of material distortion or irregularity and travel of one dielectric web with respect to the other as a result of irregularities in the winding process caused, for example, by machine wear. The dielectric webs have been offset so that each metallized edge extends outwardly. Accordingly, even if the winding machine causes a major amount of irregularity there would still be an exposed edge of metallization at the capacitor end. However, such offset is objectionable when making small sized wound capacitors, since it substantially decreases the volumetric efficiency of the capacitor. A conventional offset can increase the size of such capacitors by approximately 20%.

Also related to the size of the capacitor is the breakdown voltage. The size of a metallized film capacitor is substantially dictated by the thickness of its dielectric film. The thickness of the dielectric, in turn, is dictated by the required overall breakdown voltage of the capacitor. For instance, if a manufacturer cites a particular film as having a dielectric strength of 200 volts/$\mu$ and the capacitor design calls for a dielectric breakdown voltage of 400 volts, then the film may be 2$\mu$ thick.

The maximum electrostatic energy that can be stored in a metallized film capacitor depends on the total capacitance of the capacitor and the square of the maximum voltage that can be safely applied across the capacitor (its breakdown voltage). The breakdown voltage of a capacitor depends on the dielectric strength and the thickness of the film.

Also, related to the breakdown voltage is the number of shots a capacitor, when used as an energy storage device, can withstand. A "shot" is the two step process of (1) charging the capacitor and, then, (2) discharging the stored energy, in the form of a pulse, into a low impedance load (e.g., (1) a human body is approximately a 40 ohm load and (2) a strobe is approximately a 4 ohm load). For general applications, capacitors are rated such that they can withstand on the order of 100,000 shots; however, special applications may only require a limited number of shots.

Electrolytic capacitors have been commonly used as energy storage devices because they can be made small with high energy storage capability. However, electrolytic capacitors have many drawbacks. The drawbacks include: (1) a high dissipation factor, (2) capacitance decreases with increasing frequency, (3) capacitance substantially decreases with decreasing temperature, (4) because electrolytic capacitors are very lossy, they produce only about 80% efficiency on discharges, (5) electrolytic capacitors tend to leak and (6) if electrolytic capacitors remain idle for an extended period of time, the oxide on the aluminum must be reformed which requires precious battery power.

A particular application for which electrolytic capacitors have been used instead of metallized film capacitors, primarily because of size requirements, is in implantable defibrillators. In a recent IEEE Spectrum article, however, discussing implantable defibrillators, it was stated that "[f]uture generations of defibrillators are likely to be smaller. Today's models are about the size of a bar of soap, and shrinking them further will require new kinds of batteries and capacitors. Defibrillator manufacturers, who currently use aluminum electrolytic photoflash capacitors, are working on custom capacitors that will help reduce implant size." *IEEE Spectrum*, "Technology 1993", January 1993, pg. 76, col. 3.

In an implantable defibrillator, the capacitor is used as an energy storage device. A battery is used to charge the capacitor which, in turn, delivers a shot to the patient's heart in order to correct, for instance, ventricular tachycardia (ventricles beating to rapidly) or ventricular fibrillation (ventricle quiver chaotically). In an implantable defibrillator, the capacitor need only be capable of delivering from 3 to 6 shots. Practically speaking, if the defibrillator is unable to correct the problem within 6 shots, it is unlikely that the patient will survive, hence, eliminating the need for additional shots.

Thus, it would be advantageous, particularly for applications such as implantable defibrillators, to have metallized film capacitors which match, or even better, the size of comparable electrolytic capacitors.

SUMMARY OF THE INVENTION

The present invention involves a metallized wound capacitor having increased dielectric breakdown voltage which includes first and second dielectric webs each having a first face, a second face and a width. A first electrode having first and second portions metallized on the first face of the first web, to a width less than the width of the first web. A second electrode having first and second portions is metallized on the first face of the second web to a width less than the width of the second web. The first and second electrodes extend from opposing dielectric web longitudinal edges leaving respective bare margins along opposing edges on the respective webs. The second portion of the first electrode opposes the bare margin on the second web and the second portion of the second electrode opposes the bare margin on the first web. Each second portion has a width equal to the opposing bare margin less a predetermined tolerance and is thicker than its respective first portion. The dielectric webs are then arranged in a capacitor roll with the first and second electrodes in superposed relation to each other.

DETAILED DESCRIPTION OF THE INVENTION

A metallized film capacitor similar to the present invention is found in U.S. Pat. No. 4,420,097 issued to Lavene on Sep. 4, 1984 which is herein incorporated by reference. Also, herein incorporated by reference is the co-pending parent application, U.S. patent application Ser. No. 08/020344.

Figure 1A:
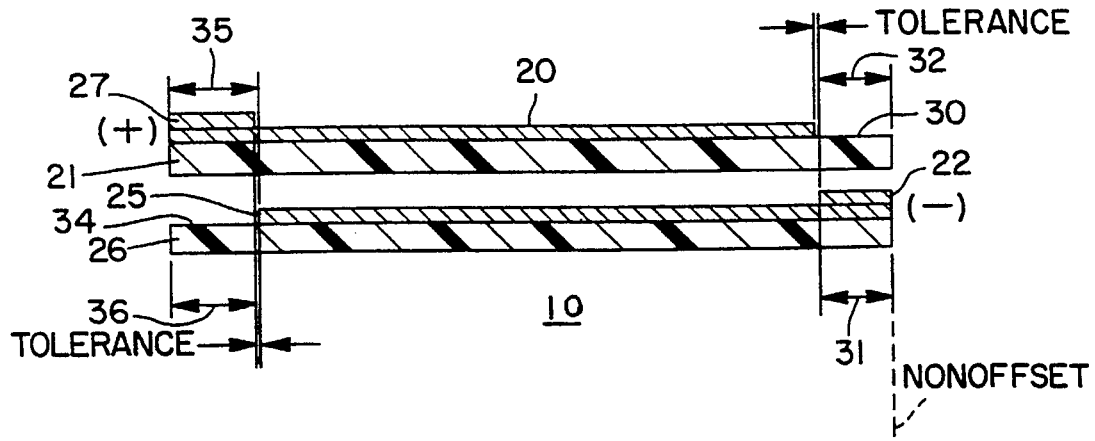
FIG. 1A is a diagramatic side elevational view of the capacitor forming non offset strips in unrolled and separated relation according to the invention.

Referring now to FIG. 1A, a non-offset capacitor 10 is shown comprising a first elongated dielectric web 21 having an electrode 20 metallized on an upper face thereof. A second elongated dielectric web 26 is aligned with and is of the same width as web 21 and also has an electrode 25 metallized on an upper face thereof. Electrodes 20 and 25 are of less width than that of webs 21 and 26 and extend from one longitudinal edge thereof leaving respective safe edges or bare margins 30, 34 of the web along opposite edges thereof. Electrode 20 extends from the left edge of web 21 and electrode 25 extends from the right edge of web 26.

In a preferred embodiment, electrodes 20, 25 are of equal width as are bare margins 30, 34. Margin 30 has a width 32 which together with the width of electrode 20 equals the total width of web 21. Similarly, margin 34 has a width 35 which together with the width of electrode 25 equals the total width of web 26.

As shown in FIG. 1A, the metallized webs 21 and 26 are disposed in superposed relation to each other with the bare margins 30, 34 respectively disposed at opposite edges of the superposed webs.

Electrodes 20 and 25 each include a second portion 27 and 22, respectively, which is relatively thicker than the remainder of the electrode. Second portions 27 and 22, for example, can be 1–4 Ohms/square; whereas, the remainder (or first portions) of electrodes 20 and 25, for example, can be 5–300 Ohms/square. The most suitable thickness for the first portions depends on the thickness (or guage) of the dielectric. For example, the following table illustrates some breakdown voltages achieved using a first portion thickness with a particular guage:

TABLE I

| DIELECTRIC THICKNESS ($\mu$) | FIRST PORTION THICKNESS (Ohms/square) | BREAKDOWN VOLTAGE (Volts) |
|---|---|---|
| 1.58 | 200 | 800 |
| 1.60 | 150 | 780 |

Although Table I only presents two examples, as can be appreciated by those skilled in the art, various thicknesses can be employed for various guages in order to achieve a desired breakdown voltage.

Second portion 22, which is directly below margin 30, extends from the right longitudinal edge of web 21 which is opposite to that edge to which electrode 20 extends. Second portion 22 is of width 31 which is equal to width 32 less a manufacturing tolerance determined by the capabilities of the metallized film converters. Therefore, in the manufacturing process, even if second portion 22 extends to its maximum tolerance width, second portion 22 would not be formed under (opposing relationship with) electrode 20. It will be understood by those skilled in the art that in the manufacturing process that the tolerance may be exceeded in some few cases and second portion 22 may undesirably extend under electrode 20.

Similarly, second portion 27, which is directly above base margins 34, extends from the longitudinal edge (left edge) remote to that edge from which electrode 25 extends. Second portion 27 is of width 36 which is equal to width 35 of margin 34 less the manufacturing tolerance, so that substantially no portion of the area of second portion 27 extends below electrode 25.

It will now be understood that since second portions 22, 27 do not extend below their respective upper electrode layers 20, 25 that there is avoided the requirement for high voltage clearing between the respective upper and lower electrodes. In accordance with the invention as a result of having a greater surface exposed to the metal spray, there is a higher probability of excellent lead termination when the terminals are formed which produces minimum ESR and minimum dissipation factor. For example, on completion of the winding of the metallized webs into a capacitor roll, relatively thicker second portion provides a thicker surface area for the metal spray. Similarly, on rolling, second portion 27 provides a thicker surface area.

On completion of the winding of capacitor roll 10, the ends may be sprayed with a high velocity mixture of compressed air and molten fine particles of tin produced from an electric arc gun. This spray forms a first terminal (not shown) in contact with second portion 22 and a second terminal in contact with second portion 27. In conventional manner leads may then be respectively bonded to the terminals.

Figure 1B:
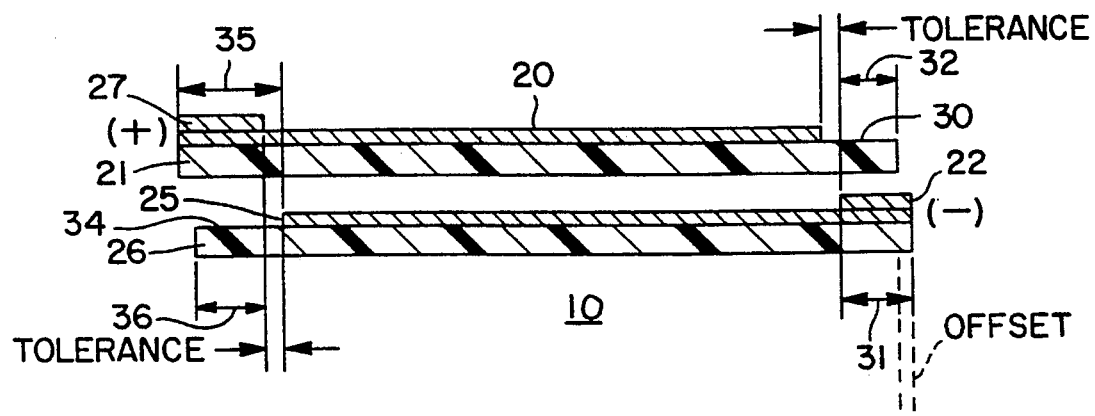
FIG. 1B is the diagramatic side elevational view of FIG. 1A with offset strips in unrolled and separated relation according to the invention.

It will now be understood by those skilled in the art that during the winding process, even though webs 21, 26 are not offset prior to winding and even if there is travel of these webs as a result of machine inconsistencies or film distortion, there will always be on each end of the capacitor exposed metallization. For example, if web 21 wanders to the right with respect to web 26, then second portion 22 is exposed at the right end so that there is a connection between a sprayed terminal and second portion 22 which electrically connects to the rest of electrode 25. It is necessary that the dimension of width 31 be such that the maximum value of such travel is no greater than that dimension. It will further be understood that if the material wander, as shown in FIG. 1B, is such that web 26 wanders to the right with respect to web 21 then electrode 25 is exposed at the right end and is directly in contact with metal spray terminal. It should be noted that an exemplary offset is 0.01 inches.

The above description applies equally to the left end of capacitor 10 in which a wandering of web 26 to the left would expose electrode 27 and a wandering of web 21 to the left would expose electrode 20. Dimension 36 is also related to the maximum travel as above described. Thus, in accordance with the present invention, nonoffset wound capacitor 10 provides an increased volumetric efficiency while still permitting sufficient exposed metallization for proper termination even if the film is distorted or the material wanders during winding. It is in this way that the volumetric efficiency is increased by the amount of reduction in offset.

In view of the above, it will now be understood that in a further embodiment of the invention, width 31 of second portion 22 is less than width 32 of the safe edge less the tolerance. Specifically, width 31 of second portion 22 may be only sufficient to meet any irregularities due to the winding machine or film distortion. Thus, even though width 31 is narrower than width 32 (less the tolerance), and web 21 wanders to the right, for example, second portion 22 would still accept a spray terminal, thereby providing an effective capacitor connection. The foregoing also applies to width 36 of second portion 27 being less than margin width 35 (less the tolerance).

Figure 2:
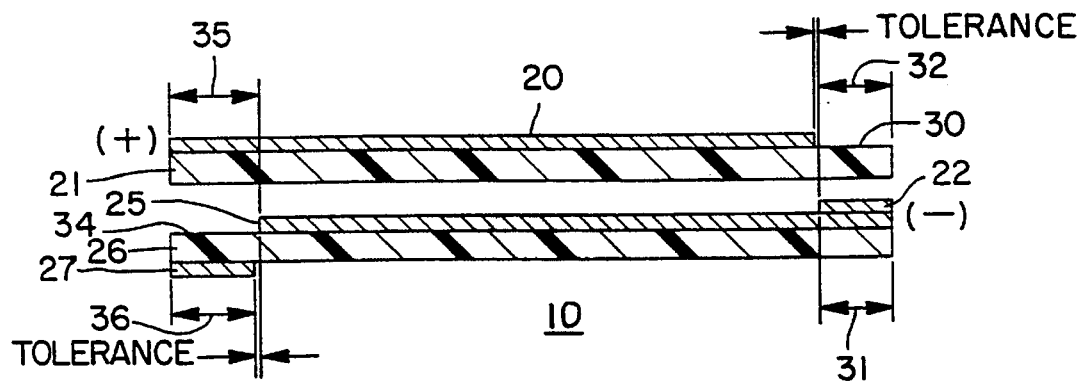
FIG. 2 is a diagramatic side elevational view of the capacitor forming non offset strips in unrolled and separated relation according to a second exemplary embodiment of the invention.

A second exemplary embodiment is shown in FIG. 2. This embodiment is the same as that described and shown in FIG. 1 except only one of the electrodes (20 or 25) includes a second relatively-thicker portion and the other electrode (25 or 20) is formed in accordance with the techniques taught in U.S. Pat. No. 4,420,097. It should be noted that the side without the relatively thicker second portion would desirably have a third electrode, as illustrated in FIG. 2, designated with reference numeral 29 and taught in the cited patent.

Figure 3:
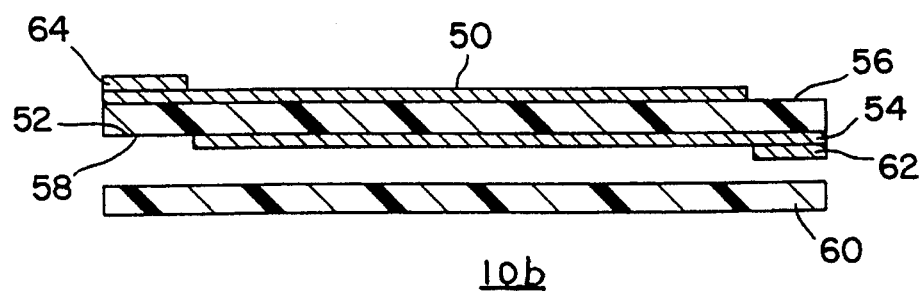
FIG. 3 is a diagramatic side elevational view of the capacitor forming non offset strips in unrolled and separated relation according to a third exemplary embodiment of the invention.

A third exemplary embodiment, shown in FIG. 3, includes a capacitor 10b which comprises a first elongated dielectric web 52 having an electrode 50 metallized on an upper face thereof. Electrode 50 extends from the left longitudinal edge of web 52 leaving a right safe edge or bare margin 56. A second electrode 54 is metallized on a lower face of web 52 and extends from the right longitudinal edge of web 52 leaving left safe edge or bare margin 58.

In accordance with this further embodiment of the invention, second web 60 is made substantially the same as and is aligned with first web 52. It should be noted that second web 60 is preferably 0.02 inches less than first web 52 in width.

Electrodes 50 and 54 each have relatively thicker second portions 64 and 62, respectively. Second portion 62, which is directly below margin 56, extends from the right longitudinal edge of web 60. Second portion 64, which is directly above margin 58, extends from the left longitudinal edge of web 60. Second portions 62, 64 are preferably about the same width as margins 56, 58 respectively.

Accordingly, in the winding of webs 60, 52, even though webs 52, 60 are of the same width, if there is travel between the webs during the winding process, there is always metallization at the respective end of the capacitor 10b. In this manner, a good electrical connection is provided with as low resistance as possible.

Although the present invention has been described with respect to details of contained embodiments thereof, it is not intended that such details be limiting upon the scope of the invention.

What is claimed:

1. A metallized wound capacitor having increased dielectric breakdown voltage comprising:

first and second elongated dielectric webs each having a first face, a second face and a width;

a first electrode having first and second portions metallized on the first face of the first web, the first electrode having a width less than the width of the first web;

a second electrode having first and second portions metallized on the first face of the second web, the second electrode having a width less than the width of the second web and said first portions of said first and second electrodes being between 5–300 ohms/square;

the first and second electrodes extend from opposing dielectric web longitudinal edges leaving respective bare margins along opposing edges on the respective webs, the second portion of the first electrode opposes the bare margin on the second web and the second portion of the second electrode opposes the bare margin on the first web, each second portion has a width equal to the opposing bare margin less a predetermined tolerance and is thicker than its respective first portion; and the dielectric webs being arranged in a capacitor roll with the first and second electrodes in superposed relation to each other.

2. A metallized wound capacitor having increased dielectric breakdown voltage comprising:

first and second elongated dielectric webs each having a first face, a second face and a width;

a first electrode having first and second portions metallized on the first face of the second web, the first electrode having a width less than the width of the first web;

a second electrode having first portion metallized on the first face of the first web, the second electrode having a width less than the width of the second web and said first portions of said first and second electrodes being between 5–300 ohms/square;

the first and second electrodes extend from opposing dielectric web longitudinal edges leaving respective bare margins along opposing edges on the respective webs, the second portion of the first electrode opposes the bare margin on the first web, the second portion has a width equal to the opposing bare margin less a predetermined tolerance, the second portion of the first electrode being thicker than its respective first portion;

a third electrode metallized on the second face of the second web, the third electrode opposes the bare margin on the first web and has a width equal to the opposing bare margin less a predetermined tolerance; and the dielectric webs being arranged in a capacitor roll with the first and second electrodes in superposed relation to each other.

3. The metallized wound capacitor of claim 1 in which said first portions of said first and second electrodes are between 70–250 Ohms/square.

4. The metallized wound capacitor of claim, in which said first portions of said first and second electrodes are between 100–200 Ohms/square.

5. The metallized wound capacitor of claim 1 in which said first portions of said first and second electrodes are substantially 200 Ohms/square for a 1.58 micron dielectric web.

6. The metallized wound capacitor of claim 1 in which said first portions of said first and second electrodes are substantially 150 Ohms/square for a 1.60 micron dielectric web.

7. The metallized wound capacitor of claim 1 in which said first portions of said first and second electrodes are sufficiently thin in order to produce a breakdown voltage of greater than 700 volts.

8. The metallized wound capacitor of claim 1 in which the webs are offset one from the other prior to being convolutely arranged in a capacitor roll.

9. The metallized wound capacitor of claim 1 in which there are provided terminals formed by metal spray at the ends of the capacitor roll in contact with the respective first electrode of one web and second electrode of the other web.

10. A metallized wound capacitor having increased dielectric breakdown comprising:

first and second elongated dielectric webs each having a first face, a second face and a width;

a first electrode having first and second portions metallized on the first face of the first web, the first electrode having a width less than the width of the first web;

a second electrode having first and second portions metallized on the second face of the first web, the second electrode having a width less than the width of the second web and said first portions of said first and second electrodes being between 5–300 ohms/square;

the first and second electrodes extend from opposing dielectric web longitudinal edges leaving respective bare margins along opposing edges, the second portion of the first electrode opposes the bare margin on the second face and the second portion of the second electrode opposes the bare margin on the first face, each second portion has a width equal to the opposing bare margin less a predetermined tolerance and is thicker than its respective first portion; and the dielectric webs being arranged in a capacitor roll with the first and second electrodes in superposed relation to each other.

11. The capacitor according to claim 1, wherein the thickness of the first portion of the first electrode is substantially the same as the thickness of the first portion of the second electrode.

12. A method for making a metallized wound capacitor having increased dielectric breakdown voltage comprising the steps of:

providing first and second elongated dielectric webs each having a first face, a second face and a width;

depositing a first electrode having first and second portions on the first face of the first web, the first electrode having a width less than the width of the first web;

depositing a second electrode having first and second portions on the first face of the second web, the second electrode having a width less than the width of the second web and said first portions of said first and second electrodes being between 5–300 ohms/square;

wherein the first and second electrodes extend from opposing dielectric web longitudinal edges leaving respective bare margins along opposing edges on the respective webs, the second portion of the first electrode opposes the bare margin on the second web and the second portion of the second electrode opposes the bare margin on the first web, each second portion has a width equal to the opposing bare margin less a predetermined tolerance and is thicker than its respective first portion; and arranging the dielectric webs in a capacitor roll with the first and second electrodes in superposed relation to each other.

13. The metallized wound capacitor according to claim 1, wherein said first portions of said first and second electrodes being greater than 14 ohms/square.

14. The metallized wound capacitor according to claim 2, wherein said first portions of said first and second electrodes being greater than 14 ohms/square.

15. The metallized wound capacitor according to claim 10, wherein said first portions of said first and second electrodes being greater than 14 ohms/square.

16. The method for making a metallized wound capacitor according to claim 12, wherein said first portions of said first and second electrodes being greater than 14 ohms/square.

17. The metallized wound capacitor according to claim 1, wherein the thickness for each second portion is 1–4 ohms/square.

18. The metallized wound capacitor according to claim 2, wherein the thickness for each second portion is 1–4 ohms/square.

19. The metallized wound capacitor according to claim 11, wherein the thickness for each second portion is 1–4 ohms/square.

20. The metallized wound capacitor according to claim 12, wherein the thickness for each second portion is 1–4 ohms/square.

* * * * *

UNITED STATES PATENT AND TRADE MARK OFFICE
CERTIFICATE OF CORRECTION

PATENT NO. : 5,608,600
DATED : March 4, 1997
INVENTOR(S) : Bernard Lavene

It is certified that error appears in the above-identified patent and that said Letters Patent is hereby corrected as shown below:

At column 7, line 1, after "claim", insert --1--.

At column 8, line 45, delete "11", and insert --10--.

Signed and Sealed this

Thirtieth Day of September, 1997

*Attest:*

BRUCE LEHMAN

*Attesting Officer*      *Commissioner of Patents and Trademarks*